United States Patent [19]

Christon et al.

[11] Patent Number: 5,722,966
[45] Date of Patent: Mar. 3, 1998

[54] WATER DISPERSIBLE AND FLUSHABLE ABSORBENT ARTICLE

[75] Inventors: Patricia Lee Christon; Nicholas Albert Ahr, both of Cincinnati, Ohio

[73] Assignee: The Procter & Gamble Company, Cincinnati, Ohio

[21] Appl. No.: 561,989

[22] Filed: Nov. 22, 1995

[51] Int. Cl.⁶ .................................................. A61F 13/15
[52] U.S. Cl. ............................................. 604/364; 604/389
[58] Field of Search ............................. 604/364, 387–391

[56] References Cited

U.S. PATENT DOCUMENTS

| | | |
|---|---|---|
| 3,078,849 | 2/1963 | Morse . |
| 3,141,051 | 7/1964 | Takai ........................... 264/219 |
| 3,407,814 | 10/1968 | George et al. . |
| 3,510,587 | 5/1970 | Marder et al. . |
| 3,542,028 | 11/1970 | Beebe et al. . |
| 3,561,447 | 2/1971 | Alexander . |
| 3,575,173 | 4/1971 | Loyer ........................... 604/387 |
| 3,636,952 | 1/1972 | George . |
| 3,665,923 | 5/1972 | Champaigne, Jr. . |
| 3,683,919 | 8/1972 | Ells . |
| 3,696,183 | 10/1972 | Steel et al. .................. 264/164 |
| 3,881,987 | 5/1975 | Benz . |
| 3,911,173 | 10/1975 | Sprague, Jr. . |
| 3,913,579 | 10/1975 | Srinivasan et al. ............ 128/290 |
| 3,950,578 | 4/1976 | Laumann . |
| 3,967,623 | 7/1976 | Butterworth et al. . |
| 4,057,061 | 11/1977 | Ishikawa et al. . |
| 4,321,924 | 3/1982 | Ahr . |
| 4,425,130 | 1/1984 | DesMarais . |
| 4,514,345 | 4/1985 | Johnson et al. . |
| 4,608,047 | 8/1986 | Mattingly . |
| 4,610,678 | 9/1986 | Weisman et al. . |
| 4,687,478 | 8/1987 | Van Tilburg . |
| 4,690,680 | 9/1987 | Higgins . |
| 4,785,996 | 11/1988 | Ziecker et al. . |
| 4,830,187 | 5/1989 | Keyes et al. . |
| 4,834,735 | 5/1989 | Alemany et al. . |
| 4,842,666 | 6/1989 | Werenicz . |
| 4,917,697 | 4/1990 | Osborn, III et al. . |
| 4,950,264 | 8/1990 | Osborn, III . |
| 5,026,363 | 6/1991 | Pratt . |
| 5,058,247 | 10/1991 | Thomas et al. . |
| 5,116,563 | 5/1992 | Thomas et al. . |
| 5,147,345 | 9/1992 | Young et al. . |
| 5,190,533 | 3/1993 | Blackburn . |
| 5,207,662 | 5/1993 | James . |
| 5,221,276 | 6/1993 | Battrell ........................ 604/391 |
| 5,230,851 | 7/1993 | Thomas . |
| 5,245,025 | 9/1993 | Trokhan et al. . |

(List continued on next page.)

FOREIGN PATENT DOCUMENTS

| | | |
|---|---|---|
| 0 198 683 A2 | 10/1986 | European Pat. Off. . |
| 0 605 016 A2 | 7/1994 | European Pat. Off. . |
| 282447 | 5/1928 | United Kingdom . |
| WO 90/03156 | 4/1990 | WIPO . |
| WO 92/02199 | 2/1992 | WIPO . |
| WO 93/09740 | 5/1993 | WIPO . |
| WO 95/03361 | 3/1994 | WIPO . |
| WO 95/16474 | 12/1994 | WIPO . |

Primary Examiner—Robert A. Clarke
Attorney, Agent, or Firm—Edward J. Milbrada; Jeffrey V. Bamber; Steven W. Miller

[57] ABSTRACT

A flushable and dispersible absorbent article is described. The absorbent article comprises a liquid pervious topsheet which preferably comprises a wet laid, apertured fibrous web having a temporary wet strength resin incorporated therein, the topsheet also having a body surface provided with a plurality of fibrils, the fibrils comprising a water resistant resinous material, a backsheet impervious to bodily fluids which preferably comprises a wet laid fibrous assembly having a temporary wet strength resin incorporated therein, the body surface of the backsheet being coated with a water resistant resinous material, an absorbent core positioned between the topsheet and the backsheet, and means for removably attaching the sanitary napkin to a wearer's undergarment. The topsheet and the backsheet are joined, at least about their periphery, using a water soluble adhesive. Alternative embodiments of the present invention can also comprise laterally extending flaps.

21 Claims, 5 Drawing Sheets

U.S. PATENT DOCUMENTS

| | | |
|---|---|---|
| 5,300,358 | 4/1994 | Evers . |
| 5,384,189 | 1/1995 | Kuroda et al. . |
| 5,405,342 | 4/1995 | Roessler et al. . |
| 5,415,643 | 5/1995 | Kolb . |
| 5,443,691 | 8/1995 | Phan et al. . |
| 5,466,337 | 11/1995 | Darlington et al. ............... 162/164.3 |
| 5,476,457 | 12/1995 | Roessler et al. . |
| 5,573,523 | 11/1996 | Whalen et al. ....................... 604/374 |
| B1 4,589,876 | 4/1993 | Van Tilburg . |

WATER DISPERSIBLE AND FLUSHABLE ABSORBENT ARTICLE

FIELD OF THE INVENTION

The present invention is directed to an absorbent article such as a sanitary napkin, panty liner, incontinence pad, or the like. More particularly, the present invention is directed to absorbent articles that may be disposed of during the flush cycle of a conventional toilet without causing disposal problems thereby.

BACKGROUND OF THE INVENTION

Disposable absorbent articles have been commercially available for many years and have met with great success world wide. A long felt need has existed for more convenient and discrete disposal methods for such absorbent articles, particularly for sanitary napkins and the like. One method that would provide such improved convenience and discretion would be the use of a conventional toilet for such disposal. However, there is a substantial risk of disposal problems, such as clogging, if commercially available sanitary napkins are disposed of by flushing them down a conventional toilet.

In the past a number of attempts have been made to provide flushable absorbent articles. British Patent No. 282, 447 attempts a partial solution by providing a core said to be flushable and a repellent treated barrier which is separated from the core and needs to be disposed of by other means. U.S. Pat. No. 3,078,849, issued to Morse on Feb. 26, 1962, describes a sanitary napkin incorporating a fluid sensitive, temporary barrier within the absorbent core for spreading bodily fluids but makes no provision for a water sensitive outer covering. U.S. Pat. No. 3,561,447, issued to Alexander on Mar. 13, 1969, describes a sanitary napkin having a nonwoven fabric covering wherein the nonwoven fabric comprises textile length fibers and the binder for the nonwoven is a combination of a soft acrylic binder and polyvinyl alcohol. This combination is said to have sufficient strength when damp to serve as an outer covering while still dispersing in water when exposed to mild agitation. While such a structure may have limited wet strength, it is unlikely that it will have sufficient barrier properties to be a satisfactory backsheet for a modern sanitary napkin. U.S. Pat. No. 3,665,923, issued to Champaigne, Jr. on May 30, 1972, describes a sanitary napkin with an wrapper comprising a nonwoven fiber web that is bonded by a water dispersible adhesive such as poly (vinyl alcohol). A preferred embodiment also comprises a baffle member of a thin impervious plastic film interposed between the absorbent pad and the wrapper. This structure solves the problem of providing barrier properties by providing a non dispersible member with the requisite barrier properties. Repeated flushing of such structures poses the risk of clogging sewer pipes because the baffle member will not disperse into small particles in a toilet. U.S. Pat. No. 5,300,358, issued to Evers on Apr. 5, 1994 describes the absorbent structures wherein the backsheet comprises two sheets of poly (vinyl alcohol) film with a highly absorbent paper structure therebetween. All surfaces that may be exposed to aqueous fluids are treated with a water repellent material, such as a fluorocarbon. The absorbent structure is also provided with a tear strip or string which, when pulled at disposal, is said to expose the highly absorbent paper structure to water which then wicks the water to the non repellent treated surfaces so they can dissolve. The requirement of a tear strip is an obvious inconvenience.

Thus, it is an object of the present invention to provide an absorbent article with performance properties (such as comfort to a wearer, leakage resistance, and the like) equaling or exceeding those of contemporary absorbent articles. It a further object of the present invention to provide absorbent articles that provide improved convenience and discretion when the used absorbent article is disposed of. It is still a further object of the present invention to provide an absorbent article that may be disposed of by flushing the article down a conventional toilet and which readily disperses into small portions when the used absorbent article is exposed to water and the mixing action of a conventional toilet.

SUMMARY OF THE INVENTION

The present invention provides an absorbent article, such as a sanitary napkin, that disperses into fragments which are readily flushable in a normal toilet. The preferred sanitary napkin of the present invention comprises a liquid pervious topsheet, a backsheet impervious to bodily fluids, an absorbent core positioned between the topsheet and the backsheet, and means for removably attaching the sanitary napkin to a wearer's undergarment. Alternative embodiments of the present invention can also comprise laterally extending flaps.

The preferred liquid pervious topsheet of the present invention comprises a wet laid apertured tissue having a temporary wet strength resin incorporated therein. Portions of the body surface of the tissue are further provided with a resinous material. Preferably, the resinous material comprises a water resistant resinous material that is provided in the form of fibrils printed on the body surface of the topsheet. Alternatively, the resinous material can provide the topsheet with a surface energy gradient between the body surface thereof and the garment surface thereof. The preferred topsheet of the present invention acquires bodily fluids at an excellent rate and serves to prevent such acquired fluids from rewetting the body surface thereof so the sanitary napkin of the present invention has a comfortable feel when it is worn.

The preferred backsheet of the present invention comprises a wet laid fibrous assembly having a temporary wet strength resin incorporated therein. The backsheet is further coated with a water resistant resinous material that causes the backsheet to become impervious to bodily fluids without impairing the spreading of adhesive materials thereon. Backsheets of the type described herein represent an improvement over those described in the art in that flushable absorbent articles of the prior art typically use materials having a very low critical surface tension to help ensure the backsheet would be impervious with resulting difficulty in adhesively joining such backsheets to the remaining components of a sanitary napkin. The backsheet of the present invention presents no such joinder issues.

The sanitary napkin is assembled by disposing the backsheet such that the surface thereof that is coated with the water resistant resinous material is oriented toward the core. The core and the topsheet are disposed thereon, and the components joined using means known to those skilled in the art. A water soluble adhesive is used to join the components of the preferred sanitary napkin of the present invention in at least an area of peripheral bonding so the components will separate when the sanitary napkin is exposed to water in a toilet.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad. A preferred embodiment of a unitary disposable absorbent article of the present invention is the catamenial pad, sanitary napkin 20, shown in FIG. 1. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external of the wearer's vestibule are also within the scope of this invention. As used herein, the term "pudendal" refers to the externally visible female genitalia. It should be understood, however, that the present invention is also applicable to other feminine hygiene or catamenial pads such as pantiliners, or other absorbent articles such as diapers, training pants, incontinence pads, and the like.

General Description of the Sanitary Napkin of the Present Invention

Figure 1:
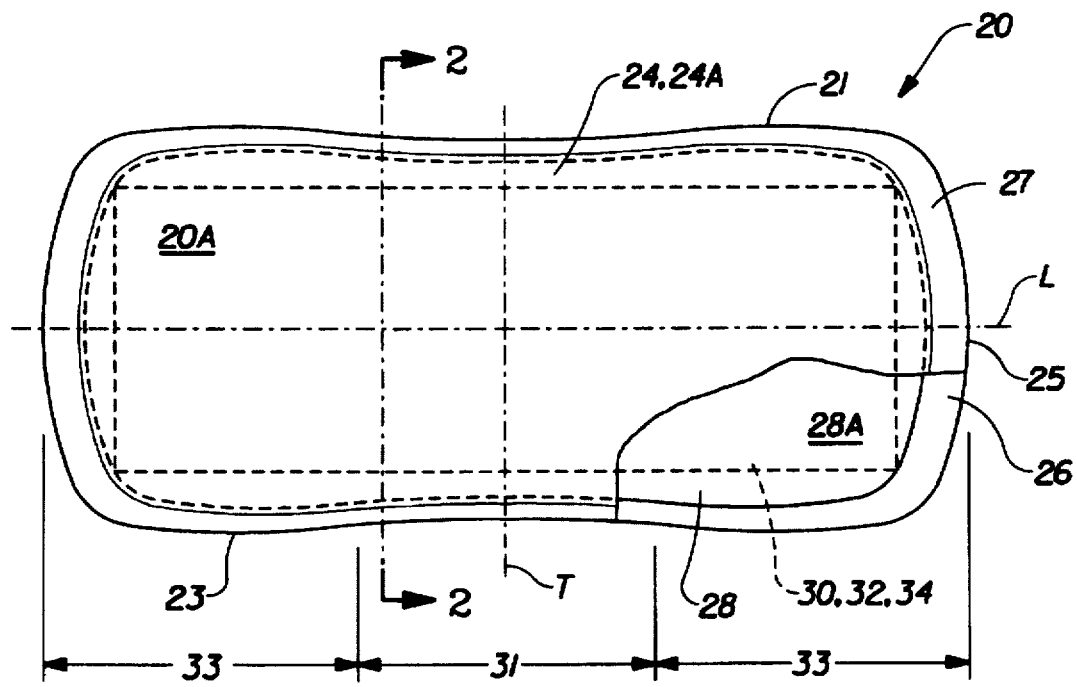
FIG. 1 is a top plan view of a preferred sanitary napkin embodiment of the present invention shown with a portion of the topsheet removed to show the underlying structure.

FIG. 1 is a plan view of the sanitary napkin 20 of the present invention in its flat-out state with portions of the structure being cut-away to more clearly show the construction of the sanitary napkin 20 and with the portion of the sanitary napkin 20 which faces or contacts the wearer, oriented towards the viewer. As shown in FIG. 1, the sanitary napkin 20 preferably comprises a liquid pervious topsheet 24, a liquid impervious backsheet 26 joined with the topsheet 24, an absorbent core 28 positioned between the topsheet 24 and the backsheet 26, and attachment means 30 for releasably attaching the sanitary napkin 20 to a wearer's undergarment.

The sanitary napkin 20 has two surfaces, a body-contacting surface or "body surface" 20A and a garment surface 20B. In a similar manner each component comprising the sanitary napkin 20 may have a body surface designated by the reference number for the component with an appended A and a garment surface designated by the reference number for the component and an appended B. The sanitary napkin 20 is shown in FIG. 1 as viewed from its body surface. The body surface 20A is intended to be worn adjacent to the body of the wearer while the garment surface 20B is on the opposite side and is intended to be placed adjacent to the wearer's undergarments when the sanitary napkin 20 is worn. The sanitary napkin 20 has two centerlines, a longitudinal centerline L and a transverse centerline T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction.

FIG. 1 also shows that the sanitary napkin 20 has a periphery 21 which is defined by the outer edges of the sanitary napkin 20 in which the longitudinal edges are designated 23 and the end edges are designated 25. A central region 31 is disposed between two end regions 33. The end regions 33 preferably extend longitudinally outwardly from the edges of the central region 31 about 12% to about 33% of the length of the sanitary napkin. A detailed description of a sanitary napkin having a central region 31 and the two end regions 33 is contained in U.S. Pat. No. 4,690,680, issued to Higgins on Sep. 1, 1987.

While the topsheet, the backsheet, and the absorbent core may be assembled in a variety of well known configurations (including so called "tube" products or side flap products), preferred sanitary napkin configurations are described generally in U.S. Pat. No. 4,950,264, issued to Osborn on Aug. 21, 1990; U.S. Pat. No. 4,425,130, issued to Desmarais on Jan. 10, 1984; U.S. Pat. No. 4,321,924, issued to Ahr on Mar. 30, 1982; U.S. Pat. No. 4,589,876, issued to Van Tilburg on Aug. 18, 1987. Each of these patents are hereby incorporated herein by reference. FIG. 1 shows a preferred embodiment of the sanitary napkin 20 in which the topsheet 24 and the backsheet 26 have length and width dimensions generally larger than those of the absorbent core 28. The topsheet 24 and the backsheet 26 extend beyond the edges of the absorbent core 28 to thereby form at least a portion of the periphery 21.

The Absorbent Core

The absorbent core 28 may be any absorbent means which is capable of absorbing or retaining liquids (e.g., menses and/or urine). As shown in FIG. 1, the absorbent core 28 has a body surface, a garment surface, side edges, and end edges. The absorbent core 28 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt.

Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core should, however, be compatible with the design loading and the intended use of the sanitary napkin. Further, the size and absorbent capacity of the absorbent core may be varied to accommodate different uses such as incontinence pads, pantiliners, regular sanitary napkins, or overnight sanitary napkins.

Exemplary absorbent structures for use as the absorbent core of the present invention are described in U.S. Pat. No. 4,950,264, issued to Osborn on Aug. 21, 1990; U.S. Pat. No. 4,610,678, issued to Weisman et al. on Sep. 9, 1986; U.S. Pat. No. 4,834,735, issued to Alemany et at. on May 30, 1989; and European Patent Application No. 0 198 683, The Procter & Gamble Company, published Oct. 22, 1986 in the name of Duenk, et al. Each of these patents are incorporated herein by reference. A preferred embodiment of the absorbent core comprises a blend of comminuted wood pulp and a superabsorbent polymer. A wood pulp suitable for comminution into airfelt is provided by the Buckeye Cellulose Corp. of Memphis, Tenn. under the designation Foley Fluff A suitable superabsorbent polymer is provided by Nalco Chemical Co. of Naperville, Ill. under the designation Nalco 1180.

The Backsheet

The backsheet 26 is impervious to bodily fluids (e.g., menses and/or urine) yet readily dispersible in cold water under the mild agitation seen when flushing a conventional toilet. As used herein, a material is impervious to bodily fluids (i.e. "water resistant") if the material is capable of capable of maintaining a hydrostatic head that is greater than about 12 cm without substantial leakage when evaluated using the method described in the TEST METHODS section below. The backsheet 26 is preferably manufactured from a wet laid tissue that also comprises a temporary wet strength resin. The tissue has also preferably been coated with a water resistant resinous material. The backsheet preferably has a matte finish to provide a more clothlike appearance. Further, the backsheet 26 may permit vapors to escape from the absorbent core 28 (i.e., breathable) while still preventing exudates from passing through the backsheet 26.

While a coated, wet laid tissue is preferred for the present invention, any fibrous assembly that is impervious to bodily fluids, yet readily dispersible in cold water under mild agitation is suitable. Thus, suitable materials include carded, air laid, or wet laid assemblies of hydrophilic fibers. Suitable fibers include, but are not limited to, natural fibers (e.g., wood or cotton fibers), synthetic fibers (e.g., polymeric fibers such as polyester, polypropylene, or polyethylene fibers) or a combination of natural and synthetic fibers. In order to ensure easy dispersibility, such fibers should be either intrinsically hydrophilic or treated to be hydrophilic. As used herein, the contact angle between water and the material surface is used to define its relative hydrophilicity.

The contact angle is less than 90 degrees for a material to be considered to be a "hydrophilic" material. Methods of treating fibrous assemblies to render them hydrophilic are described in U.S. Pat. No. 4,950,254 issued to Osborn on Aug. 21, 1990, the disclosure of which is incorporated herein by reference.

High internal phase emulsion (HIPE) foams as are described in U.S. Pat. No. 5,147,345 issued to Young, et at. on Sep. 15, 1992 are also suitable for use as a backsheet if they are treated to be impervious to bodily fluids as described below. Using HIPE foams provides the additional advantage in that HIPE foams are also capable of absorbing bodily fluids so such foams can provide at least a portion of the storage capacity of the sanitary napkin.

Figure 3:
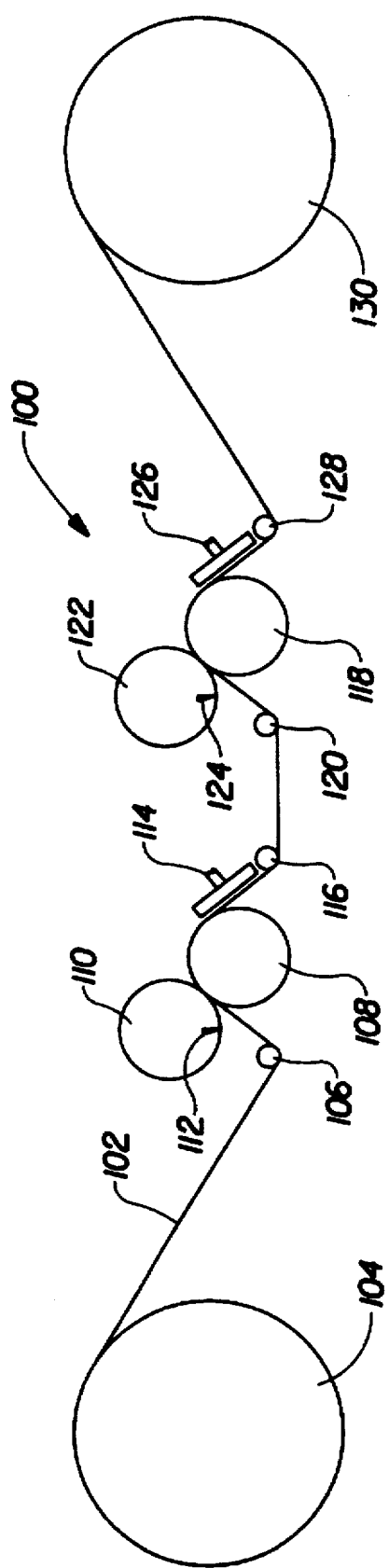
FIG. 3 is a schematic diagram of an apparatus suitable for coating the backsheet or printing the topsheet of the present invention.

Further, such fibrous assemblies as described herein should be treated to ensure they are impervious to bodily fluids. Such fibrous assemblies can be treated to be impervious to bodily fluids by a process using the resin application apparatus 100 shown in FIG. 3. As can be seen in FIG. 3, the fibrous assembly, in the form of a web of material 102, is unwound from parent roll 104. The web 102 is fed to first backing roll 108 by first feed roll 106. The water resistant resinous material (in the form of a resinous melt) is delivered to the first screen roll 110 by a first resin delivery mechanism (not shown). First doctor blade 112 is used to ensure the resinous melt is evenly metered across the entire application face of the first screen roll 110. The resinous melt is transferred from the first screen roll 110 to the web 102 using a rotary screen printing process. While rotary screen processes are well known in the art, the process described herein differs from such known processes in that the first screen roll 110 has a higher peripheral velocity than the velocity of the web of material 102 at the nip between the first screen roll 110 and the backing roll 108. This causes the first screen roll 110 to wipe the resinous material onto the web of material 102 insuring more even application of the resinous material thereon. Cooling air may be provided using first cooling air system 114 to ensure the resinous melt has solidified before the web is removed from first screen roll 110 by first stripping roll 116, if such cooling is necessary for process hygiene. The web 102 is then fed to second backing roll 118 by second feed roll 120. A second application of the resinous melt is then made using second screen roll and second doctor blade 124 in substantially the same manner as described with respect to the first screen roll 110. A two step coating process is preferred because the two step coating process provides impermeability at a lower overall level of applied water resistant resinous material than would be required for equivalent impermeability using a single step coating process. Second cooling air system 126 may be used to ensure the resinous melt has solidified as was described above with respect to first cooling air system 114. The coated web 102 is then removed from second backing roll 118 by second stripping roll and wound into finished roll 130. Tension control devices and tracking devices well known to the art may also be used as elements of this process if such devices are necessary to ensure an even coating of the water resistant resinous material across the entire transverse width of the web of material 102. This process is more fully described in U.S. Pat. No. 5,558,344, issued in the name of Ahr,et al. on Nov. 26, 1996 the disclosure of which is incorporated herein by reference.

As noted above, a preferred fibrous assembly is a wet laid tissue having a wet strength resin incorporated therein. A suitable tissue has a basis weight of about 12 pounds per 3000 square feet and is available from Georgia-Pacific Corp. of Bellingham, Wash. under the designation DST-1. Also as noted above, the wet laid tissue is preferably coated with a water resistant resinous material to render it impermeable to bodily fluids. A suitable water resistant resinous material is a hot melt resin blend which is available from Century International of Columbus, Ohio under the designation CA-105. Preferably, the coating weight is between about 0.005 grams per square inch (8 grams per square meter) and about 0.075 grams per square inch (116 grams per square meter). More preferably, the coating weight is between about 0.015 grams per square inch (23 grams per square meter) and about 0.035 grams per square inch (54 grams per square meter).

When such a wet laid tissue is coated using the resin application process described above with such a water resistant resinous material, the resulting coated web is impervious to bodily fluids. Specifically, the coated web is capable of maintaining a hydrostatic head of at least about 15 centimeters when tested as described in the TEST METHODS section. Preferably, the coated web is capable of maintaining a hydrostatic head of at least about 18 centimeters.

Not only are the coated webs of the present invention impervious to bodily fluids, they also rapidly lose mechanical integrity and dissociate into fragments on immersion in water. For example, when samples of such coated webs are evaluated for flushability using the method described in the TEST METHODS section, the coated web behaves substantially the same as a sample of a commercially available toilet tissue (CHARMIN®) used as a control. That is, the sample of the coated web of the present invention breaks up into smaller pieces that readily pass through the test apparatus with no clogging. Reduction in burst strength on exposure to water is one measure of the loss of mechanical integrity discussed above. Table 1 below shows burst strength data for a sample of the preferred backsheet 26 of the present invention.

TABLE 1

| Coated Fibrous Assembly No. | 1 |
| --- | --- |
| Fibrous Assembly Type | DST-1 |
| Resinous Coating Material | CA-105 |
| Coating Weight | 0.022 g/in$^2$ |
| Burst Strength (Grams) | |
| Dry | 1101 |
| Wet (20 Second Soak) | 477 |
| Wet Burst (20 Second)/Dry Burst | 0.43 |

As can be seen, the reduction in burst on exposure to water (forty-three percent of the dry value after 20 seconds) means that the backsheet 26 is sufficiently weakened that it will disperse into fragments under the mild agitation conditions encountered when a conventional toilet is flushed.

The backsheet 26 loses strength primarily because the water resistant resinous material no longer protects the fibrous web from water. As is noted in the Assembly of the Sanitary Napkin section below, the coated fibrous assembly that comprises the preferred backsheet 26 is disposed such that the coated surface comprises the body surface 26A of the backsheet 26. When the sanitary napkin 20 is assembled in this manner, the water resistant resinous material is disposed between the fibrous assembly of the backsheet and those components of the sanitary napkin 20 which are intended to be wet with bodily fluids such as the topsheet 24 and the absorbent core 28. Thus the coating protects the fibrous assembly from absorbed bodily fluids and the fibrous assembly provides the requisite mechanical integrity to the backsheet 26.

Using the preferred water resistant resinous material of the present invention represents an improvement over the hydrophobic materials typically used by the prior art to protect the water sensitive material comprising the backsheet (a typical prior art water sensitive material is poly (vinyl alcohol) and a typical prior art hydrophobic material is a fluorocarbon). Specifically, the hydrophobic materials used by prior art have very low critical surface tensions. For example, the critical surface tension of Teflon® is less than 20 dynes per centimeter (Adamson, A. W., *Physical Chemistry of Surfaces*, 1976, John Wiley & Sons, New York, page 354). The critical surface tension of other fluorocarbon treated surfaces is similar. This low critical surface tension means that assembly of an absorbent article will be made more difficult because a low critical surface tension interferes with adhesive bonding because adhesives will not spread on and adhere to such surfaces (Low critical surface tension is also the basis of commercially available anti-stain treatments because stains will not adhere to surfaces having a low critical surface tension). This means there is a need to either ensure that there is no fluorocarbon in areas of adhesive bonding (with the resulting manufacturing complexity of insuring adequate registration of those areas with the remaining components of a sanitary napkin) or to treat any fluorocarbon surface in an area of adhesive bonding to increase the critical surface tension thereof. Conversely, a surface coated with the preferred water resistant resinous material of the present invention has a critical surface tension of greater than about 34 dynes per centimeter when measured using the modified TAPPI test method (T 698 pm-83) described in the TEST METHODS section below. Thus, ordinary manufacturing processes can be used to assemble a sanitary napkin using the preferred backsheet of the present invention without the necessity of additional processing steps.

Thus, as used herein, a water resistant resinous material not only provides a fibrous assembly with a surface that is impervious to bodily fluids (i.e., capable of supporting a hydrostatic head of greater than about 12 cm) but also provides the coated web with a surface suitable for joining to other components using adhesive means (i.e., critical surface tension greater than about 34 dynes per centimeter).

The Topsheet

The topsheet 24 is compliant, soft feeling, and non-irritating to the wearer's skin. Further, the topsheet 24 is liquid pervious permitting liquids (e.g., menses and/or urine) to readily penetrate through its thickness. The topsheet should also be readily dispersible under the mild agitation conditions encountered when a conventional toilet is flushed. A suitable topsheet 24 may be manufactured from a wide range of materials such as air laid, wet laid, or carded nonwoven materials. Suitable materials can be comprised of natural fibers (e.g., wood or cotton fibers), synthetic fibers (e.g., polymeric fibers such as polyester, polypropylene, or polyethylene fibers) or from a combination of natural and synthetic fibers.

Figure 4:
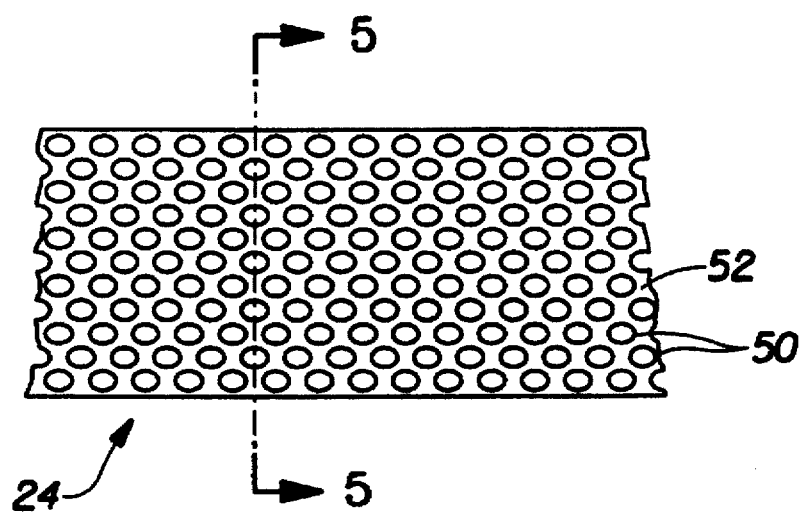
FIG. 4 is a plan view of the topsheet of the present invention.
Figure 5:
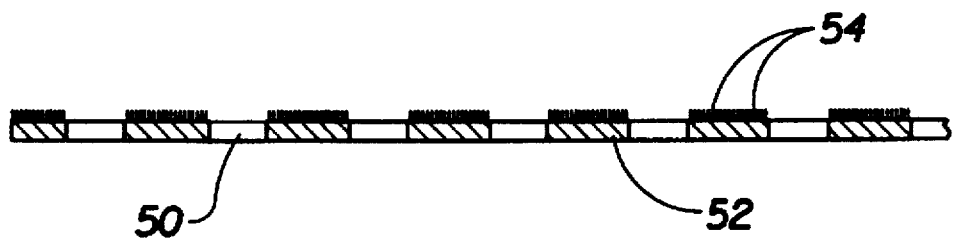
FIG. 5 is an enlarged cross-sectional view taken along line 5—5 of the topsheet of the present invention.

A preferred topsheet 24 comprises a wet laid apertured tissue having a temporary wet strength resin incorporated therein. A portion of such topsheet 26 is shown in FIGS. 4 and 5. As is shown in FIGS. 4 and 5, the wet laid tissue that comprises the preferred topsheet 26 comprises a wet laid fibrous assembly 52 having a multiplicity of apertures 50 therethrough. While a preferred fiber furnish for this tissue comprises wood fibers, preferably about 90 percent Eucalyptus fibers and about 10% Northern Sulfite Kraft fibers, other fibrous materials, including but not limited to natural fibers (e.g., other types of wood fibers or cotton fibers).

synthetic fibers (e.g., polymeric fibers such as polyester, polypropylene, or polyethylene fibers) or a combination of natural and synthetic fibers are also suitable as long as the fibers are, or can be treated to become, hydrophilic. Such a wet laid apertured tissue can be produced on a paper machine according to the method described in U.S. Pat. No. 3,881,987, issued to Benz on May 6, 1975. Preferably, the drainage member described in the aforementioned Benz patent should comprise the foraminous members described in U.S. Pat. No. 4,514,345, issued to Johnson, et al. on Apr. 30, 1985. The disclosure of each of these patents is incorporated herein by reference. The embryonic fibrous webs as would be produced as described above can be further dried using any convenient drying means as would be known to those skilled in the paper making art. For example, press felts, thermal hoods, infra-red radiation, blow-through dryers and Yankee drying drums, either used alone or in combination. A particularly preferred drying method uses a press felt and a Yankee drying drum in sequence.

The use of such a method can provide wet laid fibrous assemblies having a range of aperture densities and percent open area. As used herein, the term "aperture density" is intended to mean the number of apertures per square inch of fibrous assembly surface and the term "percent open area" is defined as that portion of the fibrous assembly surface that is not occupied by fibers expressed as a percentage. Preferably the aperture density is between about 9 apertures per square inch (1 aperture per square centimeter) and about 400 apertures per square inch (62 apertures per square centimeter). More preferably the aperture density is between about 20 apertures per square inch (3 apertures per square centimeter) and about 111 apertures per square inch (17 apertures per square centimeter). The preferred apertured wet laid fibrous assemblies of the present invention preferably have a percent open area between about 20 percent and about 50 percent. More preferably the percent open area is between about 30 percent and about 40 percent. A particularly preferred wet laid fibrous assembly has an aperture density of about 81 apertures per square inch (6 apertures per square centimeter) with about 36 percent open area.

The tissue furnish further comprises a temporary wet strength resin. Such a temporary wet strength resin helps the topsheet 24 maintain its mechanical integrity during use of the sanitary napkin 20 yet does not interfere with the dispersibility of the topsheet when the used sanitary napkin 20 is flushed. Suitable temporary wet strength resins are the glyoxalated polyacrylamide resins available from Cytec Industries Inc. of Stanford, Conn. under the designation Parez™. Particularly preferred is Parez™ 631 N.C. When Parez™631 N.C. is used at a level between about 0.5% and about 1.0% in the wet laid apertured tissue, the topsheet 26 has a satisfactory balance of mechanical integrity during use and dispersibility during disposal.

This preferred tissue is further provided with a multiplicity fibrils 54 or "hairs"on the nonapertured portion of its body facing surface. These fibrils 54 reduce the surface wetness characteristics of the topsheet 24 by separating the wearer's body from any bodily fluids that may remain on the cellulosic body side surface of the topsheet 24A. Table 2 compares the surface wetness characteristics of the topsheet 24 to the nonwoven topsheet used on a commercially available sanitary napkin (KOTEX® OVERNITES from Kimberly Clark Corp. Neenah, Wis.).

TABLE 2

| Topsheet No. | 1 | 2 |
| --- | --- | --- |
| Topsheet Type | Present Invention | Nonwoven* |
| Resinous Coating Material | CA-105 | None |
| Fibril Density | 4500 fibrils/in$^2$ | N/A |
| Surface Wetness | 0.39 g | 0.49 g |

As can be seen in Table 2, the preferred topsheet of the present invention has somewhat improved surface wetness when compared to a typical nonwoven topsheet. The fibrils 54 also provide the body surface 24A with a pleasant, velour-like tactile feel.

The fibrils 54 preferably comprise the same water resistant resinous material used to coat the backsheet 26 to render it impermeable to bodily fluids (CA-105). However, the application method described below only applies the water resistant resinous material to portions of the body surface 24A of the topsheet 24. The fibril density can vary between about 500 fibrils per square inch (77 fibrils per square centimeter to about 11,000 fibrils per square inch (1700 fibrils per square centimeter). Preferably, the fibril density is between about 3000 fibrils per square inch (450 fibrils per square centimeter and about 5000 fibrils per square inch (775 fibrils per square centimeter). Fibril length can vary between about 0.003 inches (0.07 mm) to about 0.04 inches (1.0 mm). Preferably, the fibril length is between about 0.004 inches (0.1 mm) and about 0.01 inch (0.3 mm). The Applicants have found that choice of fibril length and fibril density allows surface wetness and other topsheet characteristics, including the tactile feel, to be varied to achieve a desired balance of these characteristics.

Such fibrils 54 can be provided to the body side surface 24A by a method substantially similar to that described above for coating the backsheet 26. Referring again to FIG. 3, the main difference is that the web velocity and the peripheral velocity of the two screen rolls 110, 122 are substantially the same. This means that the CA-105 resin is printed on the web 102 rather than being wiped as described above. By control of the screen pattern on each of the screen rolls 110, 122 and of rheology of the CA-105 when it is in its melted state, the CA-105 is printed as the fibrils 54 described above. For example, heating the CA-105 to a temperature of about 121° C. (250° F.) and using screen rolls having about 100 mesh provides about 6600 fibrils per square inch of web 102 land area (1000 fibrils per square centimeter) to an apertured wet laid web 102 produced as described above. The printed, wet laid apertured tissue that is preferred for the topsheet 24, the method for producing the tissue, and the resin application method are more fully described in copending, commonly assigned U.S. patent application Ser. No. 08/561,721, filed on Nov. 22, 1995, in the names of Ahr, et al. the disclosure of which is incorporated herein by reference.

Alternatively, a wet laid apertured tissue produced according to the aforementioned U.S. Pat. No. 3,881,987 on a drainage member as described in the aforementioned U.S. Pat. No. 4,514,345 and having a wet strength resin incorporated therein may further comprise a garment surface 24B. The body surface 24A and the garment surface 24B are separated from one another by an intermediate portion 24C. The wet laid apertured tissue is treated to form a web such that the body surface of the web provides a structure which exhibits a surface energy less than the surface energy of the intermediate portion. In a preferred embodiment, the treated web exhibits a plurality of regions of comparatively low surface energy which define surface energy gradients where they interface with higher surface energy web surfaces. For example, a silicone resin having a low surface energy can be applied to portions of the body surface 24A providing such regions of comparatively low surface energy. Webs having such surface energy gradients are fully described in U.S. patent application Ser. No. 08/442,935, filed on May 31, 1995 in the name of Ouellette, et al, the disclosure of which is incorporated herein by reference.

In a preferred embodiment of the present invention, at least portions of the body surface 24A of the topsheet 24 are hydrophilic so as to help liquid to transfer through the topsheet faster than if the body surface was not hydrophilic. Such a hydrophilic surface helps to diminish the likelihood that bodily fluids will flow off the topsheet rather than flowing into and being absorbed by the absorbent core. In a preferred embodiment, surfactant is applied to the body surface 24A of the topsheet 24 (e. g. by extrusion coating or spraying) before the fibrils are printed thereon. Alternatively, the body surface of the topsheet can be made hydrophilic by treating it with a surfactant such as is described in the above referenced U.S. Pat. No. 4,950,254, the disclosure of which is incorporated herein by reference.

The Adhesive Member

In use, the sanitary napkin 20 can be held in place by any support means or attachment means 30 well-known for such purposes. Preferably, the sanitary napkin is placed in a wearer's undergarment or panty and secured thereto by a fastener such as an adhesive.

Figure 2:
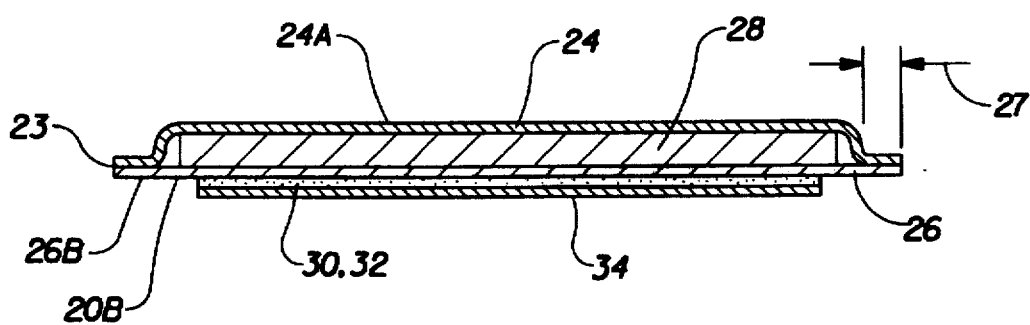
FIG. 2 is an enlarged cross-sectional view of the preferred sanitary napkin embodiment shown in FIG. 1 taken along line 2—2 of FIG. 1.

As is shown most clearly in FIG. 2, the preferred sanitary napkin 20 of the present invention further comprises an adhesive 32 for attaching the sanitary napkin 20 to a wearer's undergarment. The adhesive 20 provides a means for securing the sanitary napkin in the crotch portion of the panty by releasably adhering the sanitary napkin thereto. Thus, a portion or all of the garment surface 26B of the backsheet 26 is coated with adhesive. As can be seen most clearly in FIG. 1, the adhesive 32 is preferably provided in a rectangular pattern that coats substantially the entire garment surface 26B. It should be noted, however, that other coating patterns are also suitable. Exemplary patterns are described in copending U.S. patent application Ser. No. 08/401,665, filed on Mar. 9, 1995 in the name of Papa, et al., the disclosure of which is incorporated herein by reference.

In keeping with the objects of the present invention, any water sensitive adhesive or glue used in the art for such purposes can be used for the adhesive herein, with pressure-sensitive adhesives being preferred. Suitable adhesives are manufactured by Findley Adhesives Inc. of Wauwatosa, Wis. Particularly preferred is the hot melt adhesive available under the designation 9216-02.

In an alternative embodiment of the present invention, the attachment means can comprise the hook member of a hook and loop mechanical fastening system. Again, to be in keeping with the intent of the present invention, it is preferred that such hook attachment means comprise a water sensitive material. It has been found that, the resin (CA-105 from Century Adhesives) that comprises the fibrils 54 of the preferred embodiment of the topsheet 24 is also suitable for use in forming such hook members. Other water sensitive, thermoplastic resinous materials would also be suitable. Methods of producing such hook members and exemplary designs of such members are described in one or more of the following U.S. Patents: U.S. Pat. No. 5,058,247, issued to Thomas, et at. on Oct. 22, 1991; U.S. Pat. No. 5,116,563, issued to Thomas, et at. on May 26, 1992, and U.S. Pat. No. 5,230,851, issued to Thomas on Jul. 27, 1993 the disclosure of which is incorporated herein by reference.

Before the sanitary napkin is placed in use, the pressure-sensitive adhesive is typically covered with a removable release liner 34 in order to keep the adhesive from drying out or adhering to a surface other than the crotch portion of the panty prior to use. Suitable release liners 34 are also described in the above-referenced U.S. Pat. No. 4,917,697. Any commercially available release liners common used for such purposes can be utilized herein. Non-limiting examples of suitable release liners are BL30MG-A Silox E1/0 and BL30MG-A Silox 4P/O both of which are manufactured by the Akrosil Corporation of Menasha, Wis.

The sanitary napkin 20 of the present invention is used by removing the release liner 34 and disposing thereof in a conventional manner. Thereafter the sanitary napkin is placed in a wearer's panty so that the adhesive 32 contacts the panty. The adhesive 32 maintains the sanitary napkin in its position within the panty during use.

Assembly of the Sanitary Napkin

The topsheet 24 and the backsheet 26 are positioned adjacent the garment surface 28A and the body surface 28B, respectively, of the absorbent core 28 and are preferably joined thereto and to each other by attachment means (not shown) such as those well known in the art. For example, the backsheet 26 and/or the topsheet 24 may be secured to the absorbent core 28 or to each other by a uniform continuous layer of adhesive, a patterned layer of adhesive, or an array of separate lines, spirals, or spots of adhesive. In keeping with the objectives of the present invention, adhesives used in assembling the preferred sanitary napkin 20 should be easily disrupted by the mild agitation conditions encountered when a conventional toilet is flushed. Adhesives which have been found to be satisfactory are the hot melt adhesive available from Findley Adhesives Inc. of Wauwatosa, Wis. under the designation H-9216-02 and the adhesive emulsion available from Air Products & Chemicals Corp. of Allentown, Pa. under the designation Airflex 401. Such adhesives may be applied by gravure printing or adhesive sprays. Also suitable is adhesive application by means of an open pattern network of filaments comprising several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, or any other suitable attachment means or combinations of these attachment means as are known in the art.

As noted above and shown in FIGS. 1 and 2, in the preferred embodiment of the sanitary napkin 20 the topsheet 24 and the backsheet 26 each have length and width dimensions generally larger than those of the absorbent core 28. The topsheet 24 and the backsheet 26 extend beyond the edges of the absorbent core 28 and are joined to each other at least around the periphery 21 in an area of peripheral bonding 27 which is defined by those portions of the topsheet 24 and the backsheet 26 that extend beyond the absorbent core 28. As further noted above, the topsheet 24 is disposed such that the body surface thereof 24A is that surface provided with a multiplicity of fibrils (that is, the fibrils comprise a portion of the outer surface of the sanitary napkin 20), and the backsheet 26 is disposed such that body surface 26A is provided with the moisture resistant resinous coating (that is, the moisture resistant resinous coating is disposed on the interior of the sanitary napkin 20).

In keeping with the objects of the present invention, the topsheet 24 and the backsheet 26 are joined in the area of peripheral bonding 27 by means that are easily disrupted by the mild agitation conditions encountered when a conventional toilet is flushed. Means known to those skilled in the absorbent products art can be used to join the topsheet 24 and the backsheet 26 in the area of peripheral bonding 21 as long as such means do not interfere with the dispersibility of the sanitary napkin 20. Suitable means for joining the topsheet 24 and the backsheet 26 in the area of peripheral bonding 27 are substantially the same as those suitable for joining the topsheet 24 and/or the backsheet 26 to the absorbent core 28. Preferably, the topsheet 24 and the backsheet 26 are joined using a water soluble adhesive. Suitable adhesives include the hot melt adhesive available from Findley Adhesives Inc. of Wauwatosa, Wis. under the designation H-9216-02. A preferred water soluble adhesive is the adhesive emulsion which is available from Air Products & Chemicals Corp. of Allentown, Pa. as Airflex 401.

Depending on the form of the adhesive, the water soluble adhesive can be applied to the sanitary napkin 20 by means known to the art. For example, gravure coating, slot extrusion, and spray coating, particularly when the adhesive is applied as filaments swirled into a spiral pattern are all suitable. When used with the preferred water soluble adhesive emulsion Airflex 401 described above, gravure coating is particularly preferred.

As also noted above, the absorbent core 28 can be joined to one or both of the topsheet 24 and the backsheet 26 using a suitable water soluble adhesive. In the preferred embodiment of the present invention, the sanitary napkin 20, both the topsheet 24 and the backsheet 26 are joined to the absorbent core 28 using the preferred water soluble adhesive emulsion Airflex 401.

If desired, the preferred water sensitive garment attachment adhesive 9216-02 from Findley Adhesives Inc. of Wauwatosa, Wis. may be applied to the garment surface 26B of the backsheet 26 using slot extrusion or other suitable means and a release liner, as described above, disposed thereon.

When a sanitary napkin 20 of the present invention is assembled as described above, it will readily disperse when exposed to the mild agitation conditions encountered when a conventional toilet is flushed. For example, when such sanitary napkins are evaluated for flushability using the High Loading Protocol described in the TEST METHODS section below they flush in substantially the same manner as a commercially available toilet tissue ((CHARMIN®). These results can be explained by the following model:

1) The water soluble adhesive joining the topsheet, the absorbent core and the backsheet rapidly dissolves allowing the components of the sanitary napkin 20 to separate.

2) This separation exposes protected portions of these components to the water with a resulting decrease in the mechanical strength of these components.

3) The components further disperse into smaller particles that pass through the test apparatus similarly to a toilet tissue (CHARMIN®) control Optional Features
Flaps In an alternative embodiment of the present invention, the sanitary napkin has two flaps each of which are adjacent to and extend laterally from the side edge of the absorbent core in at least the central region. The flaps are configured to drape over the edges of the wearer's panties in the crotch region so that the flaps are disposed between the edges of the wearer's panties and the thighs. The flaps serve at least two purposes. First, the flaps help serve to prevent soiling of the wearer's body and panties by menstrual fluid, preferably by forming a double wall barrier along the edges of the panty. Second, the flaps are preferably provided with attachment means on their garment surface so that the flaps can be folded back under the panty and attached to the garment facing side of the panty. In this way, the flaps serve to keep the sanitary napkin properly positioned in the panty. The flaps can be constructed of various materials including materials similar to the topsheet, backsheet, tissue, or combination of these materials. Further, the flaps may be a separate element attached to the main body of the napkin or can comprise extensions of the topsheet and backsheet (i.e., unitary). A number of sanitary napkins having flaps suitable or adaptable for use with the sanitary napkins of the present invention are disclosed in U.S. Pat. No. 4,687,478, which issued to Van Tilburg on Aug. 18, 1987; U.S. Pat. No. 4,589,876, which issued to Van Tilburg on May 20, 1986; and U.S. Pat. No. 4,608,047, which issued to Mattingly on Aug. 26, 1986. The disclosure of each of these patents is incorporated herein by reference.

TEST METHODS

Burst Strength

Overview

The test specimen, held between annular clamps, is subjected to increasing force that is applied by a 0.625 inch diameter, polished stainless steel ball. The burst strength is that force that causes the sample to fail. Burst strength may be measured on wet or dry samples.

Apparatus

Burst Tester Intelect-II-STD Tensile Test Instrument, Cat. No. 1451-24PGB or the Thwing-Albert Burst Tester are both suitable. Both instruments are available from Thwing-Albert Instrument Co., Philadelphia, Pa. The instruments must be equipped with a 2000 g load cell and, if wet burst measurements are to be made, the instruments must be equipped with a load cell shield and a front panel water shield.

Conditioned Room Temperature and humidity should be controlled to remain within the following limits:

Temperature: 73±3_F. (23° C.±2° C.)

Humidity: 50±2% Relative Humidity

Paper Cutter Scissors or other equivalent may be used

Pan For soaking wet burst samples, suitable to sample size

Solution Water for soaking wet burst samples should be equilibrated to the temperature of the conditioned room.

Timer Appropriate for measuring soak time

Sample preparation

1) Cut the sample to a size appropriate for testing (minimum sample size 4.5 in×4.5 in). Prepare a minimum of five samples for each condition to be tested.

2) If wet burst measurements are to be made, place an appropriate number of cut samples into a pan filled with temperature-equilibrated water.

Equipment Setup

1) Set the burst tester up according to the manufacturer's instructions. If an Intelect-II-STD Tensile Test Instrument is to be used the following are appropriate:

Speed: 12.7 centimeters per minute

Break Sensitivity: 20 grams

Peak Load: 2000 grams

2) Calibrate the load cell according to the expected burst strength.

Measurement and Reporting

1) Operate the burst tester according to the manufacturer's instructions to obtain a burst strength measurement for each sample.

2) Record the burst strength for each sample and calculate an average and a standard deviation for the burst strength for each condition.
3) Report the average and standard deviation for each condition to the nearest gram.

Flushability

Overview

As used herein, the term "flushability" is defined as a product's capacity to pass through typical commercially available household toilets and plumbing drainage systems without causing clogging or similar problems that can be directly associated with the physical characteristics of the product. More specifically, catamenial products are evaluated for flushability via relative ease of toilet bowl and trap evacuation and subsequent transport through a simulated plumbing system.

The test procedure is designed to simulate two days of normal toilet usage for a family of 4 (2 men, 2 women). The test employs a flushing sequence to simulate the following conditions: male urination visits, female urination visits (including post urinary drying with tissue), disposal of catamenial product with cleaning using tissue, and bowel movement visits. The amount of tissue to be used for each tissue flush is a normal loading of 2 strips of seven sheets, or the High Loading of 5 strips of seven sheets. The normal loading is based on consumer research regarding typical habits and practices and the high loading is 2.5 times the normal loading. The test is designed to simulate the conditions a product will encounter if it is flushed through a conventional toilet and into a municipal sewer or into a septic tank. Samples are evaluated for: 1) toilet bowl and trap clearance, 2) drain line blockage, and 3) disintegration during flushing.

Apparatus

Figure 6:
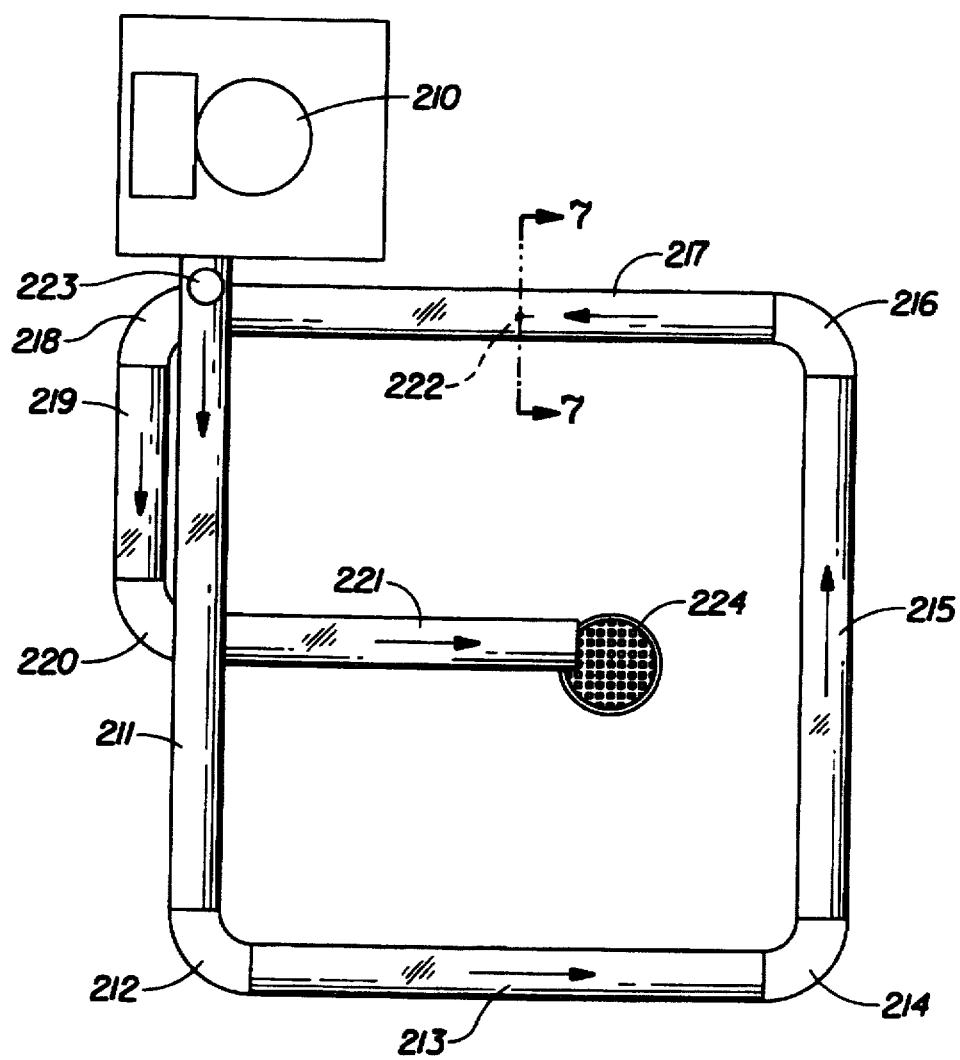
FIG. 6 is a plan view of an apparatus suitable for flushability determination according to the method described in the TEST METHODS section below.
Figure 7:
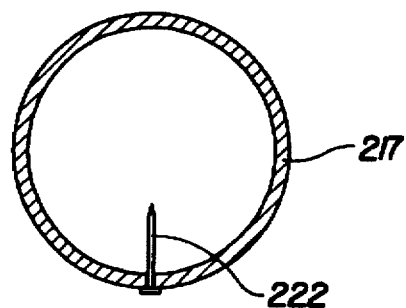
FIG. 7 is a cross section of the flushability apparatus of FIG. 6 taken along line 8—8 thereof.

An apparatus suitable for the flushability test is shown in plan view in FIG. 6. The apparatus includes:

- a 3.5 gallon (13.2 liter) water saver siphon vortex toilet referred to as 210 (additional toilets can also be attached to the piping layout shown in FIG. 6 to evaluate the behavior of test samples using different flushing mechanisms such as commercial, pressure toilets);
- approximately 59 feet (18 meters) of 4 inch (10 cm) id acrylic pipe (As can be seen from FIG. 6, the piping is assembled in roughly a square configuration having linear runs 211,213,215, 217, 219, 221 approximately 10 feet (3 meters) long);
- a cast iron tee 223 slightly downstream of the toilet 210 that is open to the atmosphere for venting;
- five cast iron ninety degree elbows 212, 214, 216, 218, and 220;
- a snag 222 positioned vertically (FIG. 7) approximately 15 feet from the pipe's terminal end and approximately 1 inch (2.5 cm) long; and
- a screen (No. 4 Tyler sieve) to capture solid effluent for evaluation of disintegration.

The apparatus used for this method is set up to be equivalent to ANSI Standard A112.19.2M-1990 for Vitreous China fixtures. The piping is plumbed to provide a drop of 0.25 inch per foot (2 centimeters/meter) of pipe length.

Materials

Control Tissue Product: CHARMIN®

Synthetic Fecal Material

Prepared according to the method described below

Test Flushing Sequence

The test flushing sequence simulates 2 days of normal toilet usage for a family of 4 (2 men, 2 women; based on consumer habits and practices research). The sequence of 34 total flushes consists of 14 flushes with an empty bowl, 8 flushes with tissue only, 6 flushes with tissue and a catamenial product and 6 flushes with tissue and simulated fecal matter (SFM). When it is used, the SFM is placed in the bowl just prior to the addition of tissue. The SFM loading of 160 g±5 g consists of two 1 inch (2.5 centimeter) ×4 inch (10 centimeter) pieces and one 1 inch (2.5 centimeter) ×2 inch (5 centimeter) piece. Folded tissue strips (or the catamenial product) are placed in the bowl at 10 second intervals. Ten seconds after the final strip or pad is placed into the bowl, the toilet is flushed. The flushing sequence is described below as a series of two routines combined in the following order:

Routine #1 (To be performed 6 times for a total of 30 flushes)

1) Flush With Tissue Only —Take a drain line blockage reading 2 minutes after the water reaches the simulated obstruction, wait 1 additional minute, and move to step 2.

2) Flush With Empty Bowl. Take a drain line blockage reading 2 minutes after the water reaches the snag point and move to step 3.

3) Flush With Tissue and Pad—Take a drain line blockage reading 2 minutes after the water reaches the snag point, wait 1 additional minute, and move to step 4.

4) Flush With Empty Bowl. Take a drain line blockage reading 2 minutes after the water reaches the snag point and move to step 5.

≡)Flush With Tissue and Simulated Fecal Mater (SFM). Take a drain line blockage reading 2 minutes after the water reaches the snag point, wait 1 additional minute.

Routine #2 (To be performed 1 time)

1) Flush With Tissue Only —Take a drain line blockage reading 2 minutes after the water reaches the snag point, wait 1 additional minute, and move to step 2.

2) Flush With Empty Bowl. Take a drain line blockage reading 2 minutes after the water reaches the snag point and move to step 3.

3) Flush With Tissue Only —Take a drain line blockage reading 2 minutes after the water reaches the snag point, wait 1 additional minute, and move to step 4.

4) Flush With Empty Bowl. Take a drain line blockage reading 2 minutes after the water reaches the snag point.

Total number of flushes per sequence is 34.

If, at any point in the flushing sequence, the product remains in the bowl or trap after flushing, the tissue and or pad is plunged into the drainage line manually and the flushing sequence will continue. After completion of each trial loading, the drainage pipe will be cleared prior to beginning subsequent testing.

The above-described flushing sequence is repeated three times for each test product and three times for each control product.

Data Reporting

The degree of drain line blockage is determined by measuring the length of water dammed up behind the obstruction. Graduations are marked every 12 inches (30 centimeters) on the drainpipe upstream of the obstruction. Each one foot length that the water is backed up corresponds to 0.25 inch (0.6 centimeter) or 6.25% of blockage at the obstruction point. Test product residues which exit the drainpipe are also collected.

The following data are recorded for each evaluation:

1) Incidence of failure to clear bowl and trap

2) Incidence of labored (difficult), but successful bowl and trap clearing

3) Incidence of product on simulated snag

4) Maximum level (%) of drain line blockage

5) Cumulative level (%) of drain line blockage over 2 days.

Preparation of Synthetic Fecal Material

I. Materials Needed

Feclone synthetic fecal matter (900 grams); (Available from Siliclone Studio, Valley Forge, Pa. as product BFPS-dry concentrate )

Tap water at 100° C. (6066 grams)

II. Equipment Needed

Mixer (Available from Hobart Corp., Troy, Ohio as Model A200)

Extruder (Available from Hobart Corp., Troy, Ohio as Model 4812)

Disposable Centrifuge tubes with screw caps (50 ml) (Available from VWR Scientific, Chicago, Ill. as Catalog No. 21-008-176)

Water Bath to control temperature to 37° C.

III. Preparation

1. Pour the 100° C. water into the mixing bowl of the mixer and add the dry Feclone concentrate.

2. Mix on low for 1 minute.

3. Mix on medium speed for 2 minutes.

4. After the material is well mixed, transfer to the extruder.

5. Using an ice pick, punch a small hole in the tip of each centrifuge tube.

6. Extrude the Feclone into the centrifuge tubes.

7. Cap the centrifuge tubes and store in the refrigerator.

8. Before using, put the tubes in the water bath at 38° C.

Hydrostatic Head

Overview

The height of a column of water over a sample of material that can be supported with no visual evidence of fluid transport through the sample.

Apparatus

Conditioned Room Temperature and humidity should be controlled to remain within the following limits:

Temperature: 73±3_F. (23° C.±2° C.)

Humidity: 50±2% Relative Humidity

Figure 8:
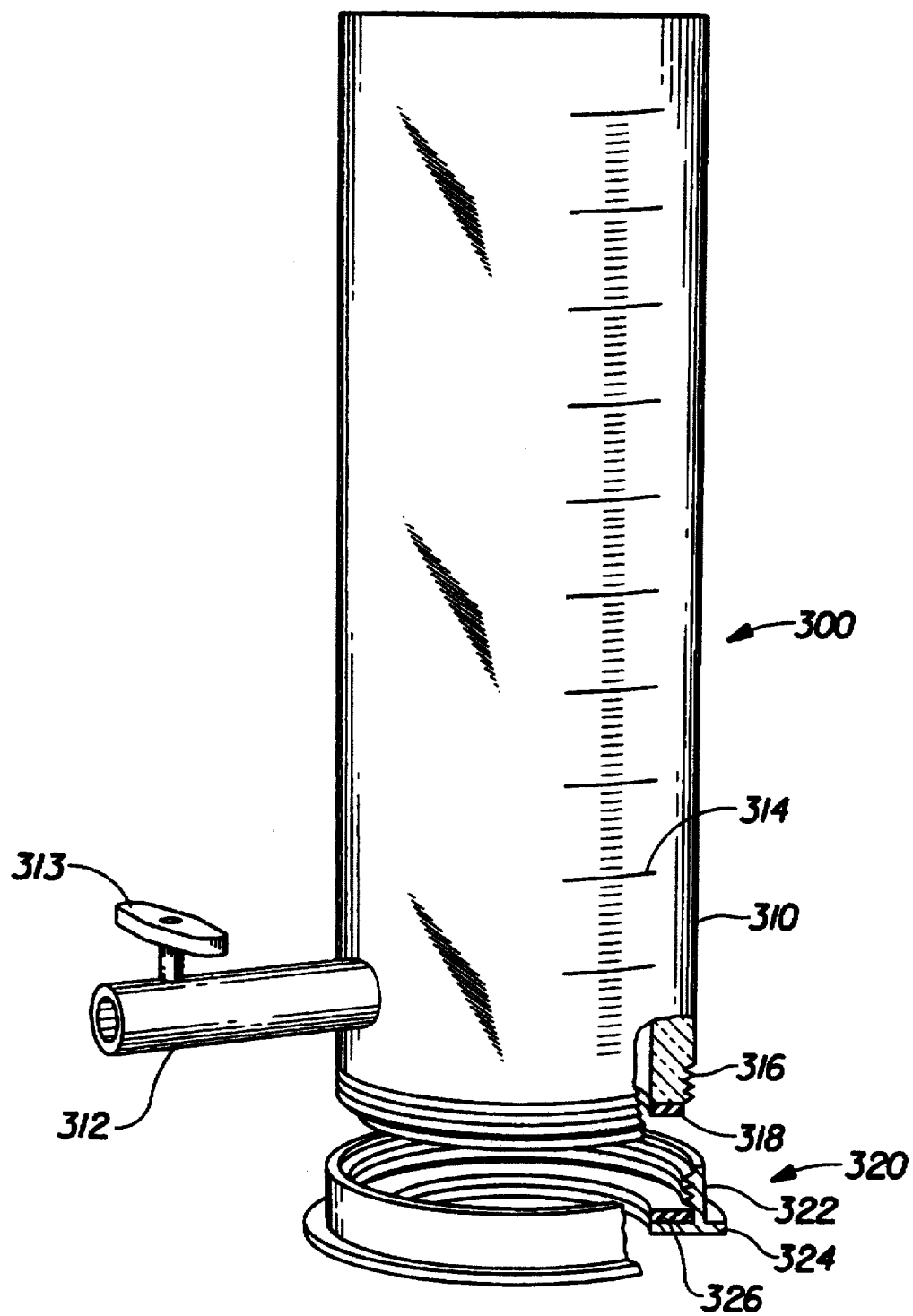
FIG. 8 is a perspective view showing the assembly of the apparatus used to measure hydrostatic head.

Test Apparatus The test apparatus is shown in FIG. 8 and comprises:

a water vessel 300 which comprises:

1. a glass tube 2.125 inch (0.84 cm) diameter identified as 310;

2. a fill tube 312 adapted to deliver water (source not shown) at a controlled rate into the glass tube 310;

3. on/off valve 313 for controlling whether water is delivered to the water vessel 300;

4. indicia 314 scribed into the surface of the glass tube 310 adapted to allow measurement of the hydrostatic head to an accuracy of ±1 centimeter;

5. a male fitting 316 adapted to receive the sample holder 320; and 6. an annular rubber gasket 318 positioned beneath the lower end of the glass tube 310; and a sample holder 320 which comprises:

1. a female fitting 322;

2. an annular sample support 324 joined to the lower edge of the female fitting 322; and 3. an annular rubber gasket 326.

Ring Stand For holding the test apparatus in a vertical position and Clamp

Mirror Placed beneath the sample holder 320 to aid in seeing water penetration of the sample Method 1. Assemble the apparatus, using a ring stand and clamp to hold the water vessel 300 in a vertical orientation and connecting an adjustable water source to the supply tube 312. 2. Adjust the water temperature to 73° F. ±2° F. (23° C.±1 C.). 3. Insert a water impervious blank (e.g., polyethylene film) into the sample holder 320, screw the sample holder 320 onto the water vessel 300, open the on/off valve 313, adjust the water flow (adjustment means not shown in FIG. 8) so the hydrostatic head rises at a rate of 1 inch per minute±0.1 inch per minute (2.5 centimeters per minute±0.25 centimeters per minute), and close the on/off valve 313. 4. Die cut a circular sample 2.625 inches in diameter and insert the sample into the sample holder 320. For backsheet samples of the preferred embodiment of the present invention the surface that has been provided with the water resistant resin should be placed facing upward. (The sample should be placed in the conditioned room at least 2 hours prior to testing.). 5. Screw the sample holder 320 onto the water vessel 300 being careful not to crease the sample. Tighten the sample holder only enough to insure that there are no leaks around the sample. 6. Place the mirror under the sample holder 320. 7. Start the water flow into the water vessel 300 by opening the on/off valve 313. 8. Observe the exposed surface of the sample by watching the mirror. Signs of water penetration include beading and spreading of a visible color change on the bottom surface of the sample. 9. Record the height of the column of water when penetration is first observed as the hydrostatic head for the sample. 10. Repeat the measurement 5 times and report the average and standard deviation of the measurements.

Surface Wetness

Overview

Surface wetness is a test designed to measure the amount of liquid which emerges from an absorbent structure, such as the sanitary napkin 20 shown in FIG. 1, through a topsheet to cause wetness on the surface of the topsheet. The amount of moisture drawn through the topsheet is termed "surface wetness" and serves as an estimate of how dry the wearer's skin would remain if placed in contact with the absorbent structure.

Method

The test comprises wetting a 4 inch (10 centimeter) ×4 inch (10 centimeter) sample of a topsheet material while superposed, body surface 24A facing up, on a standardized absorbent element preferably comprising a layer of airlaid comminuted wood pulp fibers enveloped between a pair of wet strength tissue plies with a simulated urine solution (available from Jayco Pharmaceuticals, Mehcanicsburg, Pa.). The simulated urine solution (4.0±0.3 ml) is delivered to the surface of the sample using a syringe pump. A uniform pressure loading of 0.25 psi (1.7 kPa), is applied to each sample while the simulated urine is being delivered so that the fluid is uniformly distributed throughout the sample. After all of the simulated urine has been delivered, the wetted sample is allowed to sit undisturbed for 5±0.5 minutes. The sample is covered with polyethylene film to minimize evaporation while the sample is sitting. The pressure is momentarily removed. A preweighed sample of filter paper (7 plies) approximately 5 inches (12 centimeters)×5 inches (12 centimeters) is inserted over the uppermost surface of the topsheet of the absorbent sample (Suitable filter paper is available from Ahlstrom Filtration Company of Mt. Holly springs, Pa. as Paper No 632). Sufficient weight to apply a predetermined pressure loading of 0.5 psi (3.4 kPa) is applied to the sample for a period of 15±1 seconds and removed. The filter paper is then removed and reweighed The amount of fluid absorbed by the filter paper is termed the "surface wetness" of the sample. Results are expressed in grams of fluid absorbed by the filter paper. As should thus be apparent, a lower "surface wetness" number is indicative of dryer surface feel.

Critical Surface Tension

The method described in TAPPI (Technical Association of the Pulp and Paper Industry) method T 698 pro-83, "Determination of Wetting Tension of Polyethylene and Polypropylene Films (modified visking analytical technique)" was used substantially as described therein with the exception that a commercially available series of known surface tension liquids (available from Corotec Corporation, Collinsville, Conn.) was used instead of the mixtures described in the TAPPI method and brushes, as supplied with the Corotec series were used instead of the cotton swabs.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A water dispersible and flushable absorbent article, the absorbent article comprising:
   a liquid pervious topsheet comprising a first fibrous assembly having a temporary wet strength resin incorporated therein; a dispersible liquid impervious backsheet disposed beneath said topsheet, said backsheet comprising a water insoluble second fibrous assembly having a temporary wet strength resin incorporated therein that has been coated on at least one surface with a second resinous material wherein said second resinous material is water resistant; and
   an absorbent core disposed between said topsheet and said backsheet wherein said topsheet and said backsheet are joined using a water soluble adhesive in at least an area of peripheral bonding to encapsulate said absorbent core therebetween.

2. The absorbent article of according to claim 1 wherein portions of a body surface of said topsheet have been provided with a first resinous material.

3. The absorbent article of claim 2 wherein said first resinous material comprises fibrils of a water resistant resinous material.

4. The absorbent article of claim 3 wherein said first resinous material comprises a silicone resin.

5. The absorbent article of claim 2 wherein said portions of said first resinous material comprise fibrils of a water resistant resin.

6. The absorbent article of claim 5 wherein said fibrils are provided at a density of between about 3000 fibrils per square inch and about 5000 fibrils per square inch.

7. The absorbent article of claim 6 wherein said absorbent article further comprises a water sensitive adhesive disposed on said body surface of said backsheet.

8. The absorbent article of claim 5 said backsheet has a body surface and a garment surface and said second resinous material enables said backsheet to resist a hydrostatic head of at least about 18 cm and provides said body surface of said backsheet with a critical surface tension of greater than about 34 dynes per centimeter.

9. The absorbent article of claim 5 wherein said second resinous material is applied at a coating weight of between about 0.020 grams per square inch and about 0.25 grams per square inch.

10. The absorbent article of claim 1 wherein said first fibrous assembly and said second fibrous assembly comprise a wet laid tissue.

11. The absorbent article of claim 10 wherein said first assembly is apertured.

12. The absorbent article of claim 1 wherein said portions of said body surface provide a plurality of regions of comparatively low surface energy.

13. The absorbent article of claim 1 wherein said absorbent article further comprises a means for attaching said absorbent article to a wearer's undergarment.

14. The absorbent article of claim 13 wherein said means for attaching said absorbent article comprises a water sensitive adhesive.

15. The absorbent article of claim 13 wherein said means for attaching said absorbent article comprises a hook member wherein said hook member comprises a water resistant resinous material.

16. The absorbent article of claim 1 wherein said temporary wet strength resin comprises a glyoxalated polyacrylamide resin.

17. The absorbent article of claim 1 wherein said absorbent article delaminates into its components and said components disperse into fragments when said absorbent article is immersed in water and the water is mildly agitated.

18. A water dispersible and flushable sanitary napkin, the sanitary napkin comprising:
   a liquid pervious topsheet comprising a wet laid apertured tissue having a temporary wet strength resin incorporated therein wherein portions of a body surface of said topsheet have been provided with fibrils comprising a first resinous material;
   a dispersible, liquid impervious backsheet disposed beneath said topsheet, said backsheet comprising a water insoluble wet laid tissue having a temporary wet strength resin incorporated therein that has been coated on at least one surface with a second resinous material wherein said second resinous material is water resistant; and
   an absorbent core disposed between said topsheet and said backsheet wherein said topsheet and said backsheet are joined using a water soluble adhesive in at least an area of peripheral bonding to encapsulate said absorbent core therebetween.

19. The sanitary napkin of claim 18 wherein said fibrils are provided at a density of between about 3000 fibrils per square inch and about 5000 fibrils per square inch and said wet laid apertured tissue has between about 20 apertures per square inch and about 111 apertures per square inch therein.

20. The sanitary napkin of claim 19 wherein said second resinous material enables said backsheet to resist a hydrostatic head of at least about 18 cm and provides said body surface of said backsheet with a critical surface tension of greater than about 34 dynes per centimeter.

21. The sanitary napkin of claim 19 wherein said absorbent article further has longitudinal and transverse centerlines and a pair of longitudinally oriented sides and said sanitary further comprises at least one flap which is joined to one of said sides and extends transversely outwardly therefrom.

* * * * *